United States Patent [19]

Jones et al.

[11] Patent Number: 5,763,654

[45] Date of Patent: Jun. 9, 1998

[54] PROCESS FOR THE PRODUCTION OF ACETIC ACID BY THE CARBONYLATION OF DIMETHYL ETHER

[75] Inventors: Michael David Jones; Andrew David Poole, both of East Riding, United Kingdom

[73] Assignee: BP Chemicals Limited, London, England

[21] Appl. No.: 731,313

[22] Filed: Oct. 15, 1996

[30] Foreign Application Priority Data

Oct. 20, 1995 [GB] United Kingdom ............... 9521501

[51] Int. Cl.$^6$ .................. C07C 51/10; C07C 51/12; C07C 53/08
[52] U.S. Cl. .................. 562/517; 562/519; 562/607
[58] Field of Search ............ 562/517, 519, 562/607

[56] References Cited

U.S. PATENT DOCUMENTS

| | | | |
|---|---|---|---|
| 3,769,329 | 10/1973 | Paulik et al. | 560/232 |
| 3,772,380 | 11/1973 | Paulik et al. | 560/232 |
| 4,417,000 | 11/1983 | Slaugh et al. | 518/713 |
| 5,003,104 | 3/1991 | Paulik et al. | 562/517 |
| 5,189,203 | 2/1993 | Hansen et al. | 560/232 |
| 5,286,900 | 2/1994 | Hansen et al. | 560/232 |
| 5,510,524 | 4/1996 | Garland et al. | 562/519 |

FOREIGN PATENT DOCUMENTS

| | | |
|---|---|---|
| 1167064 | 5/1984 | Canada . |
| 079461 | 5/1983 | European Pat. Off. . |
| 0 566 370 | 10/1993 | European Pat. Off. . |
| 566371 | 10/1993 | European Pat. Off. . |
| 0 643 034 | 3/1995 | European Pat. Off. . |
| 1234641 | 6/1971 | United Kingdom . |
| 2 206 349 | 1/1989 | United Kingdom . |

*Primary Examiner*—Gary Geist
*Assistant Examiner*—Rosalynd Keys
*Attorney, Agent, or Firm*—Fay, Sharpe, Beall, Fagan, Minnich & McKee

[57] ABSTRACT

A process for the production of acetic acid which comprises reacting carbon monoxide with a carbonylatable reactant comprising greater than 10%, typically from 30 to 100%, by weight dimethyl ether introduced to a reactor in which there is maintained at elevated temperature a liquid reaction composition comprising a Group VIII noble metal catalyst, for example rhodium or iridium, methyl iodide promoter, an optional co-promoter and water at a concentration in the liquid reaction composition of from 1.0 to 10% by weight.

12 Claims, No Drawings

PROCESS FOR THE PRODUCTION OF ACETIC ACID BY THE CARBONYLATION OF DIMETHYL ETHER

The present invention relates to a process for the production of acetic acid by the carbonylation of a carbonylatable reactant comprising dimethyl ether.

Hydrocarbonylation involving the reaction of dimethyl ether, acetic acid, hydrogen and carbon monoxide to form ethylidene diacetate is described in European patent publications EP 0566370-A2 and EP 0566371-A2. According to these patent applications the catalyst system consists essentially of a Group VIII metal, methyl iodide, lithium iodide and optionally lithium acetate. The reaction is said to be preferably run using a 1:1 to 4:1 molar ratio of carbon monoxide to hydrogen. Although water may be added to the reactor feed, the final reaction conditions are essentially anhydrous.

The carbonylation of dimethyl ether/methanol mixtures prepared from synthesis gas is described in U.S. Pat. Nos. 5,189,203 and 5,286,900. The products of the carbonylation process are said to be acetic acid, methyl acetate and/or acetic anhydride depending upon whether water is also fed to the reactor. Homogeneous or heterogeneous catalysts are said to be usable; however, in the experimental examples only heterogeneous rhodium on activated carbon is used. No indication of the benefits to liquid-phase carbonylation rate of using dimethyl ether are given.

U.S. Pat. No. 3,769,329 relates to a process for the reaction of alcohols and the ester, ether and halide derivatives thereof, with carbon monoxide in the presence of catalyst systems containing as active constituents a rhodium component and a halogen component to yield carboxylic acids and/or esters selectively and efficiently. U.S. Pat. No. 3,772,380 relates to a similar process in which the active constituents of the catalyst system are an iridium component and a halogen component. In both U.S. Pat. No. 3,769,329 and U.S. Pat. No. 3,772,380 dimethyl ether is listed as one of a number of a suitable feed materials for the carbonylation reaction. The use of methanol feedstock containing 10 weight percent dimethyl ether is described in Example 19 of U.S. Pat. No. 3,769,329 and Example 19 of U.S. Pat. No. 3,772,380; however, the use of such a mixed feedstock is merely said to have no deleterious effect on the reaction.

GB 1234641 relates to a process for the treatment of a reactant selected from an alcohol, halide, ester, ether or phenol with carbon monoxide to give organic acids and/or esters in the presence of a catalyst comprising a noble metal component selected from iridium, platinum, palladium, osmium and ruthenium and their compounds, and a promoter substance which is said to be a halogen or a halogen compound. It is stated in GB 1234641 that dimethyl ether, as a by-product, is undesirable because it suppresses the carbon monoxide partial pressure and ultimately causes a decrease in the desired carbonylation reaction rate. Example 7 of GB 1234641 relates to an iridium catalysed reaction in which a methanol feedstock containing 10% by weight dimethyl ether is carbonylated at a carbon monoxide partial pressure of about 700 psig and at a reaction temperature of 175° C. in the presence of methyl iodide promoter. This example is said to demonstrate that an impure alcohol feedstock having ether in the alcohol has no deleterious effect on the reaction.

None of the above patents teach that using dimethyl ether as feed to a liquid-phase carbonylation reaction has any beneficial effect on the carbonylation rate.

It has now been unexpectedly found that in the production of acetic acid by liquid phase carbonylation in the presence of a Group VIII noble metal catalyst, methyl iodide promoter and a finite concentration of water the reaction rate of dimethyl ether carbonylation can be greater than that of methyl acetate and/or methanol.

Thus, according to the present invention there is provided a process for the production of acetic acid which process comprises reacting carbon monoxide with a carbonylatable reactant introduced to a reactor in which there is maintained at elevated temperature a liquid reaction composition comprising a Group VIII noble metal catalyst, methyl iodide promoter, an optional co-promoter, and at least a finite concentration of water characterised in that the carbonylatable reactant comprises greater than 10% by weight dimethyl ether and the concentration of water in the liquid reaction composition is from 0.1 to 10% by weight.

The carbonylatable reactant comprises greater than 10% by weight dimethyl ether, typically between 30 and 100% by weight dimethyl ether, for example from 50 to 100% by weight dimethyl ether.

Preferably, the carbonylatable reactant comprises dimethyl ether together with methanol and/or methyl acetate. Preferably, the carbonylation reactant comprises dimethyl ether and methanol.

In the production of acetic acid by the liquid phase carbonylation of dimethyl ether in the presence of a Group VIII noble metal catalyst, methyl iodide promoter and a finite concentration of water, reaction might be expected to proceed by strong acid catalysed hydrolysis (for example by HI formed in situ) of dimethyl ether. The methanol formed in situ by strong acid catalysed hydrolysis of dimethyl ether together with any methanol co-reactant would be predominantly converted to methyl acetate in the liquid reaction composition by reaction with acetic acid product or solvent. The equilibrium between an ester and an alcohol is described in Organic Chemistry John McMurry, p 777, Brooks/Cole, 1984, 1st Ed where the ester is said to be favoured at high alcohol or low water concentrations.

A carbonylatable reactant comprising dimethyl ether and methanol may suitably be obtained by reacting a mixture of carbon monoxide and hydrogen in the presence of a methanol synthesis catalyst and a methanol dehydration catalyst. Alternatively the reactant may be obtained by reacting carbon monoxide with hydrogen in the presence of a methanol synthesis catalyst in a first step and thereafter reacting a part of the methanol formed in the first step with a methanol dehydration catalyst in a second step. Preferably, the carbonylatable reactant comprising dimethyl ether and methanol is obtained from synthesis gas (a 1:1 molar mixture of carbon monoxide and hydrogen). Preferably, the methanol synthesis catalyst is a conventional catalyst comprising copper oxide and zinc oxide supported on alumina. Preferably, the methanol dehydration catalyst is an acid catalyst, more preferably a zeolite catalyst such as ZSM-5. Suitable processes for the production of a carbonylatable reactant comprising dimethyl ether are described for example in U.S. Pat. No. 5,286,900, U.S. Pat. No. 5,189,203 and U.S. Pat. No. 4,417,000.

Water may be formed in situ in the liquid reaction composition, for example, by the esterification reaction between methanol formed in situ by hydrolysis of dimethyl ether/methanol co-reactant and acetic acid product/acetic acid solvent. However, water is also consumed in situ in the liquid reaction composition when dimethyl ether is hydrolysed to methanol. Water may also be introduced to the carbonylation reactor either together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water in the liquid reaction composition is from 1 to 10%, more preferably from 1 to 8%, by weight.

The process of the present invention has been found to be particularly beneficial for the production of acetic acid at relatively low water concentrations. Under these conditions the process of the present invention has the advantage of providing increased rate of carbonylation and/or increased catalyst stability over processes which do not employ dimethyl ether as reactant. For both rhodium- and iridium-catalysed liquid phase carbonylation as hereinbefore mentioned the water concentration is preferably from 1 to 10% by weight, more preferably from 1 to 8% by weight. It has been found that for carbonylation of reactants comprising greater than 10% by weight dimethyl ether with rhodium catalysts such low water concentrations can be achieved without the need to use a co-promoter such as a group IA or IIA metal iodide, a quaternary ammonium iodide or a phosphonium iodide.

Preferably, the Group VIII noble metal catalyst in the liquid reaction composition comprises a rhodium- or an iridium-containing compound which is soluble in the liquid reaction composition. The rhodium- or iridium-containing compound may be added to the liquid reaction composition in any suitable form which dissolves in the liquid reaction composition or is convertible to a soluble form.

Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-$, $[Ir(CO)_2Br_2]^-$, $[Ir(CO)_2I_2]^-$, $[Ir(CH_3)I_3(CO)_2]^-$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Preferred are chloride-free complexes of iridium such as acetates, oxalates and acetoacetates.

Preferably, the concentration of the iridium-containing compound in the liquid reaction composition is in the range 100 to 6000 ppm by weight of iridium.

Examples of suitable rhodium-containing compounds which may be added to the liquid reaction composition include $[Rh(CO)_2Cl]_2$, $[Rh(CO)_2I]_2$, $[Rh(Cod)Cl]_2$, rhodium III chloride, rhodium III chloride trihydrate, rhodium III bromide, rhodium III iodide, rhodium III acetate, rhodium dicarbonylacetylacetonate, $RhCl_3(PPh_3)_3$ and $RhCl(CO)(PPh_3)_2$.

Preferably, the concentration of the rhodium-containing compound in the liquid reaction composition is in the range 10 to 1500 ppm by weight of rhodium.

When the Group VIII noble metal catalyst is iridium, the optional co-promoter may be selected from the group consisting of ruthenium, osmium, rhenium, cadmium, mercury, zinc, gallium, indium and tungsten. The optional co-promoter may comprise any ruthenium-, osmium-, rhenium-, cadmium-, mercury-, zinc-, gallium-, indium- or tungsten-containing compound which is soluble in the liquid reaction composition. The optional co-promoter may be added to the liquid reaction composition of the carbonylation reaction in any suitable form which dissolves in the liquid reaction composition or is convertible to soluble form.

Examples or suitable ruthenium-containing compounds which may be used as optional co-promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $RuI_2(CO)_4$, tetra(aceto) chlororuthenium (II,III), ruthenium (III) acetate, ruthenium (III) propionate, ruthenium (III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium (II), tetrachlorobis(benzene)diruthenium(II), dichloro(cycloocta-1,5-diene)ruthenium (II) polymer and tris(acetylacetonate)ruthenium (III).

Examples of suitable osmium-containing compounds which may be used as optional co-promoter include osmium (III) chloride hydrate and anhydrous, osmium metal, osmium tetraoxide, triosmiumdodecacarbonyl, pentachloror-μ-nitrododiosmium and mixed osmium halocarbonyls such as $OsI_2(CO)_4$, tricarbonyldichloroosmium (II) dimer and other organoosmium complexes.

Examples of suitable rhenium-containing compounds which may be used as optional co-promoter include $Re_2(CO)_{10}$, $Re(CO)_5Cl$, $Re(CO)_5Br$, $Re(CO)_5I$, $ReCl_3.xH_2O$ and $ReC_5.yH_2O$.

Examples of suitable cadmium-containing compounds which may be used as optional co-promoter include $Cd(OAc)_2$, $CdI_2$, $CdBr_2$, $CdCl_2$, $Cd(OH)_2$ and cadmium acetylacetonate.

Examples of suitable mercury-containing compounds which may be used as optional co-promoter include $Hg(OAc)_2$, $HgI_2$, $HgBr_2$, $Hg_2I_2$, and $HgCl_2$.

Examples of suitable zinc-containing compounds which may be used as optional co-promoter include $Zn(OAc)_2$, $Zn(OH)_2$, $ZnI_2$, $ZnBr_2$, $ZnCl_2$, and zinc acetylacetonate.

Examples of suitable gallium-containing compounds which may be used as optional co-promoter include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used as optional co-promoter include indium acetylacetonate, indium acetate, $InCl_3$, $InBr_3$, $InI_3$, $InI$ and $In(OH)_3$.

Examples of suitable tungsten-containing compounds which may be used as optional co-promoter include $W(CO)_6$, $WCl_4$, $WCl_6$, $WBr_5$, $WI_2$, $C_9H_{12}W(CO)_3$ or any tungsten chloro-, bromo, or iodo-carbonyl compound.

Preferably, both the iridium- and optional co-promoter compounds are sodium free.

The molar ratio of each optional co-promoter:iridium catalyst is in the range (0.1 to 20):1.

When the Group VIII noble metal catalyst is rhodium, the optional co-promoter may be selected from ruthenium, osmium, rhenium and manganese. Examples of suitable ruthenium-, osmium-, or rhenium-containing compounds are as described above. Examples of suitable manganese-containing compounds which may be used include $Mn_2(CO)_{10}$, manganese (II) acetate, manganese (II) bromide, manganese (II) bromide tetrahydrate, manganese (II) chloride, manganese (II) chloride hydrate, manganese (II) iodide, manganese (II) oxide, manganese (III) oxide, manganese (IV) oxide, $Mn(CO)_5Br$ and $Mn(CO)_5I$.

The molar ratio of each optional co-promoter:rhodium catalyst is suitably in the range (0.1 to 20):1, except for manganese:rhodium which is in the range (0.2 to 20:1).

When the Group VIII noble metal catalyst is rhodium, the optional co-promoter may also be selected from the group consisting of Group IA and Group IIA metal iodides, quaternary ammonium iodides and phosphonium iodides. The concentration of the optional co-promoter in the liquid reaction composition is preferably equivalent, up to 20% by weight of lithium iodide.

The promoter is methyl iodide. When the group VIII noble metal catalyst is iridium, the concentration of methyl iodide in the liquid reaction composition is preferably in the range of 1 to 20% by weight, preferably 2 to 15% by weight. When the Group VIII noble metal catalyst is rhodium, the concentration of methyl iodide in the liquid reaction composition is preferably in the range 1 to 30% by weight, preferably 1 to 20% by weight, more preferably 5 to 20% by weight.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, as its presence may result in the formation of hydrogenation products.

When the Group VIII noble metal catalyst is rhodium the pressure of the carbonylation reaction is suitably in the range 1 to 100 barg, preferably 20 to 50 barg. The temperature of the carbonylation reaction is suitably in the range 130° to 250° C., preferably in the range 170° to 200° C.

When the Group VIII noble metal catalyst is iridium the pressure of the carbonylation reaction is suitably in the range 10 to 200 barg, preferably 10 to 100 barg, most preferably 15 to 50 barg. The temperature of the carbonylation reaction is suitably in the range 100° to 300° C., preferably in the range 150° to 220° C.

Acetic acid may be used as a solvent for the reaction.

The process of the present invention may be performed as a batch or a continuous process, preferably as a continuous process.

The acetic acid product may be removed from the reactor by withdrawing liquid reaction composition and separating the acetic acid product by one or more flash and/or fractional distillation stages from the other components of the liquid reaction composition such as iridium or rhodium catalyst, optional co-promoter, methyl iodide, water and unconsumed reactants which may be recycled to the reactor to maintain their concentrations in the liquid reaction composition. The acetic acid product may also be removed as a vapour from the reactor.

The invention will now be illustrated by way of example only be reference to the following examples. In Examples 1 and 2 and Experiments A–D the following method and apparatus were employed:

A 150 ml Hastelloy B2 (Trade Mark) autoclave equipped with a Magnedrive (Trade Mark) stirrer, an injection port and cooling coils was used for a series of batch carbonylation experiments employing methyl acetate or dimethyl ether as feed. For each batch carbonylation experiment employing methyl acetate as feed, a liquid injection facility was connected to the injection port of the autoclave. For each batch carbonylation experiment employing dimethyl ether as feed, a Whitey (Trade Mark) sample bomb was connected to the injection port of the autoclave. A gas supply to the autoclave was provided from a gas ballast vessel, feed gas being provided to maintain the autoclave at a constant pressure and the rate of gas uptake being calculated (with an accuracy believed to be +/−1%) from the rate at which the pressure falls in the gas ballast vessel. The pressures used in batch autoclave experiments for dimethyl ether carbonylation may be generally higher than might be expected to be used in a continuous process because of the need to have sufficient carbon monoxide partial pressure, particularly for the iridium catalysed system.

For each batch carbonylation experiment in which dimethyl ether was used as feed and iridium as catalyst, the autoclave was charged with optional co-promoter, the iridium catalyst and the liquid components of the liquid reaction composition excluding the dimethyl ether feed.

Dimethyl ether was pre-charged to the Whitey (Trade Mark) bomb by transferring an amount of dimethyl ether which exceeded the required weight of feed from a cylinder (supplied by Aldrich) to the bomb which was pre-weighed and chilled in cardice. The bomb was slowly vented until the desired weight of dimethyl ether feed was retained in the bomb and was then connected to the injection port of the autoclave.

The autoclave was flushed twice with nitrogen and once with carbon monoxide and the autoclave sealed. The contents of the autoclave were then heated with stirring (1000 rpm) to the desired reaction temperature. After allowing the system to stabilise for about 30 minutes, the dimethyl ether feed was transferred to the autoclave by over-pressurising the bomb with carbon monoxide and then opening the injection port of the autoclave. The pressure in the autoclave was subsequently maintained at the desired reaction pressure with carbon monoxide fed on demand from the gas ballast vessel.

For each batch carbonylation experiment in which dimethyl ether was used as feed and rhodium as catalyst the above procedure was employed except that the catalyst was not charged to the autoclave with the liquid components and promoter of the liquid reaction composition excluding the dimethyl ether feed. Instead, the rhodium catalyst in aqueous acetic acid was introduced to the autoclave by means of a Gilson (Trade Mark) HPLC pump connected to an inlet valve on the autoclave immediately prior to introducing the dimethyl ether feed to the autoclave.

For each batch carbonylation experiment in which methyl acetate was used as feed the above procedure was employed except that methyl acetate was charged to the autoclave together with optional co-promoter, and the components of the liquid reaction composition excluding part of the acetic acid and/or water charge in which the rhodium and iridium catalyst was dissolved.

After allowing the system to stabilise for about 30 minutes, the rhodium or iridium catalyst solution was injected into the autoclave through the liquid injection facility under pressure of carbon monoxide.

Reactions employing dimethyl ether and methyl acetate as feed were compared under conditions such that the amount of carbon monoxide consumed, if the reactions proceeded to completion, would be the same. Furthermore, the final liquid reaction compositions would be expected to be the same. The starting compositions for the batch carbonylation experiments were calculated by considering the following equilibria:

| 2 Methyl acetate + 2 H$_2$O | = 2 Methanol + 2 Acetic acid | (1) |
| --- | --- | --- |
| 2 Methanol | = Dimethyl ether + H$_2$O | (2) |
| 2 Methyl Acetate + H$_2$O | = Dimethyl ether + 2 Acetic acid | (3) |

Thus, the molar amount of dimethyl ether feed required to replace an amount of methyl acetate feed can readily be calculated by considering Equation (3). For example, 2 moles of methyl acetate and 1 mole of water in a liquid reaction composition should be replaced with 1 mole of dimethyl ether and 2 moles of acetic acid.

Gas uptake from the ballast vessel was measured every 30 seconds and from this was calculated the rate of carbonylation, expressed as mmoles of carbon monoxide per hour (mmol/hr). After uptake of carbon monoxide from the ballast vessel had ceased or the reaction had proceeded for 40 minutes, whichever was sooner, the autoclave was isolated from the gas supply. The contents of the autoclave were cooled to room temperature and the gases were cautiously vented from the autoclave, sampled and analysed by gas chromatography. The liquid reaction composition was discharged from the autoclave, sampled and was analysed for liquid products and by-products by gas chromatography.

To obtain a reliable baseline a number of identical baseline runs may have to be performed to condition the autoclave such that consistent rates are achieved. This conditioning period is often different from autoclave to autoclave.

Experiment A

A baseline experiment was performed with a rhodium catalyst without promoter at a high water concentration (decreasing from an initial charge of 17.0% by weight to a calculated value of 11.6% by weight assuming 100% conversion of substrate). The rate of carbon monoxide uptake from the ballast vessel was calculated to be 628 mmol/hr and this rate remained constant throughout the course of the reaction until all the methyl acetate substrate was consumed. This experiment is not an example according to the present invention because dimethyl ether was not used as feed to the carbonylation reaction.

Experiment B

Experiment A was repeated (water concentration decreasing from 14.4 to 11.6% by weight as above) except that dimethyl ether was used as feed, the amount of dimethyl ether employed being calculated using Equation (3) above. The rate of carbon monoxide uptake from the ballast vessel was calculated to be 610 mmol/hr. The rate of carbon monoxide uptake remained constant throughout the course of the reaction. This experiment is not an example according to the present invention because greater than 10% by weight water in the reaction composition was employed. It demonstrates when compared with Experiment A that at high water concentrations (i.e. greater than 10% by weight) in the reaction mixture improvement in the carbonylation rate is not obtained when dimethyl ether is substituted for methyl acetate as feed in an amount greater than 10% by weight of the feed.

Experiment C

A baseline experiment was performed at a lower (decreasing from 5.1 to 0.5% by weight as above) water concentration than employed in Experiment A. The rate of carbon monoxide uptake from the ballast vessel measured after 5 minutes was found to be 594 mmol/hr. The rate of gas uptake was found to constantly decrease during the course of the reaction as the water concentration steadily reduced, this was believed to be a consequence of progressive catalyst deactivation at low water concentrations. This experiment is not an example according to the present invention because no dimethyl ether was used as feed to the carbonylation reaction.

EXAMPLE 1

Experiment C was repeated (water concentration decreasing from 2.8 to 0.4% by weight as above) except that dimethyl ether was used as feed, the amount of dimethyl ether employed being calculated using Equation (3). The rate of carbon monoxide uptake from the ballast vessel after 5 minutes was found to be 350 mmol/hr. In contrast to Experiment C, no reduction in the rate of carbon monoxide uptake was observed during the reaction. This example is according to the present invention and shows that the use of dimethyl ether at low water concentrations has a beneficial effect on the stability of a rhodium catalyst without the need to use a co-promoter such as an iodide salt, for example lithium iodide.

Experiment D

A baseline experiment was performed (water concentration decreasing from 10.8 to 2.7% by weight as above) using an iridium catalyst and a ruthenium co-promoter with methyl acetate as feed to the carbonylation reaction. The rate of gas uptake from the ballast vessel after 5 minutes was found to be 1615 mmol/hr. This is not an example according to the present invention because no dimethyl ether was used as feed to the carbonylation reaction.

EXAMPLE 2

Experiment D was repeated (water concentration decreasing from 7.0 to 2.7% by weight as above) except that dimethyl ether was used as feed, the amount of dimethyl ether being calculated using Equation (3). The rate of uptake of carbon monoxide from the ballast vessel after 5 minutes was found to be 1969 mmol/hr. This example is according to the present invention and demonstrates that increased carbonylation rates can be achieved by employing dimethyl ether as feed to a carbonylation reaction.

The autoclave charges, reaction temperatures and pressures for Experiments A–D and Examples 1 and 2 are given in Table 1. Analyses of the non-condensable gases vented from the autoclave at the end of the experiment are given in Table 2. Analyses of the liquid reaction compositions at the end of the experiments revealed that acetic acid was the major product (greater than 99% by weight) for all experiments.

TABLE 1

Autoclave charge and Reaction Conditions.

| Experiment | Feed | Temp (°C.) | Pressure (barg) | Run Time (min) | MeOAC (mmol) | DME (mmol) | MeI (mmol) | Water (mmol) | AcOH (mmol) | Ir (mmol) | Ru (mmol) | Rh (mmol) |
|---|---|---|---|---|---|---|---|---|---|---|---|---|
| Experiment A | MeOAc | 185 | 27.5 | 27.5 | 244 | — | 101 | 772 | 744 | — | — | 0.40[a] |
| Experiment B | DME | 185 | 27.8 | 27.5 | — | 122 | 102 | 622 | 981 | — | — | 0.40[b] |
| Experiment C | MeOAc | 185 | 27.8 | 40 | 244 | — | 101 | 272 | 894 | — | — | 0.20[c] |
| Example 1 | DME | 185 | 27.3 | 40 | — | 124 | 101 | 7 | 1164 | — | — | 0.40[d] |
| Experiment D | MeOAc | 190 | 38.0 | 23 | 389 | — | 41 | 261 | 739 | 0.94[e] | 0.62[f] | — |
| Example 2 | DME | 190 | 38.2 | 20.5 | — | 195 | 41 | 346 | 477 | 0.94[g] | 0.63[f] | — |

[a]$RhCl_3.3H_2O$ dissolved in 139 mmol water and 42 mmol acetic acid.
[b]$RhCl_3.3H_2O$ dissoved in 167 mmol water and 50 mmol acetic acid.
[c]$Rh_2(CO)_4Cl_2$ dissolved in 83 mmol acetic acid.
[d]$RhCl_3.3H_2O$ dissolved in 139 mmol water and 58 mmol acetic acid.
[e]$IrCl_3.3H_2O$ dissolved in 278 mmol water.
[f]$Ru_3(CO)_{12}$.
[g]$IrCl_3.3H_2O$.

TABLE 2

Analyses of Non-Condensable Gases

| Experiment | Methane (% v/v) | CO$_2$ (% v/v) | DME (% v/v) |
|---|---|---|---|
| Experiment A | 0.2 | 2.6 | — |
| Experiment B | 0.3 | 2.2 | 1.5 |
| Experiment C | trace | trace | — |
| Example 1 | 2.0 | — | — |
| Experiment D | 4.4 | 2.9 | — |
| Example 2 | 4.3 | 1.9 | 5.1 |

Balance comprises hydrogen (not measured), nitrogen and carbon monoxide.

High Pressure Infrard Cell Experiments

The following experiments were performed with a high pressure infrared cell. In these experiments rates were based on total gas uptake and no attempt was made to compensate for partitioning of dimethyl ether between gas and liquid phases.

Experiment E—Carbonylation of methyl acetate with rhodium catalyst

The following solution was charged to high pressure infrared cell.

| Cell charge | |
|---|---|
| Methyl acetate | 4.70 g |
| Methyl iodide | 3.60 g |
| Water | 1.28 g |
| Acetic acid | 13.29 g |
| Injector charge | |
| Acetic acid | 2.00 g |
| [Rh(CO)$_2$Cl]$_2$ | 0.025 g |

The solution was flushed and pressured with carbon monoxide and heated to 185° C. where the catalyst was injected with carbon monoxide so that the total pressure in the cell was 30 barg. The pressure was maintained by feeding carbon monoxide from a ballast vessel and the reaction was monitored by measuring the pressure drop in the ballast vessel. Infrared spectra of the rhodium species present was recorded throughout the reaction. When gas uptake had stopped the product solution was analysed by gas chromatography.

The carbonylation rate was initially linear followed by a steady decrease in rate corresponding to a decrease in the active catalytic species [Rh(CO)$_2$I$_2$]$^-$ and an increase of the inactive catalytic species [Rh(CO)$_2$I$_4$]$^-$.

| Calculated methyl acetate concentration (%) | Carbonylation rate (mol/hr) | Rh as Rh(CO)$_2$I$_2$ (%) |
|---|---|---|
| 18.4 | 0.161 | 100 |
| 15 | 0.151 | 88 |
| 10 | 0.126 | 70 |
| 5 | 0.092 | 50 |
| 1 | 0.023 | 17 |

This is not an example according to the present invention because no dimethyl ether was used as feed to the carbonylation reaction.

EXAMPLE 3

Carbonylation of Dimethyl Ether With Rhodium Catalyst

Experiment D was repeated as above using dimethyl ether in place of methyl acetate.

| Cell charge | |
|---|---|
| Dimethyl ether | 1.47 g |
| Water | 0.69 g |
| Acetic acid | 18.14 g |
| Injector charge | |
| Methyl iodide | 3.75 g |
| [Rh(CO)$_2$Cl]$_2$ | 0.025 g |

The carbonylation rate was 0.169 mol/hr and this was linear until close to the end of the reaction. The rhodium catalyst was present totally as [Rh(CO)$_2$I$_2$]$^-$.

In contrast with Experiment E this is an example according to the present invention because dimethyl ether was present in the feed. It demonstrates that the rate of carbon monoxide uptake is accelerated by the presence of dimethyl ether at low water levels and that the catalyst is stabilised.

Experiments F and G and Examples 4 and 5 were carried out in an analogous manner to those described in Experiments A–D and Examples 1 and 2 with the exception that a 300 mL Hastelloy B2 (Trade Mark) autoclave was used. Also a dual liquid injection facility connected to the injection port of the autoclave allowed introduction of either Rh or Ir catalyst followed by DME substrate by use of an over pressure of carbon monoxide gas as described in previous examples. Furthermore, gas uptake from the ballast vessel was measured every 2 seconds rather than every 30 seconds as described in previous examples.

Experiment F

A baseline experiment was performed (water concentration decreasing from 9.7 to 1.6% by weight during the course of the reaction assuming 100% conversion of substrate) using an iridium catalyst with methyl acetate as a feed to the carbonylation reaction. The rate of gas uptake from the ballast vessel after 5 minutes was found to be 2226 mmol/hr. This is not an example according to the present invention because no dimethyl ether was employed.

EXAMPLE 4

Experiment F was repeated (water concentration decreasing from 5.7 to 1.6% by weight as above) except that dimethyl ether was used as a feed, the amount used being calculated using Equation (3). The rate of carbon monoxide uptake after 5 minutes was found to be 2722 mmol/hr. This example, which is according to the present invention, demonstrates faster carbonylation rates can be achieved by using dimethyl ether as a feed to a carbonylation reaction, as opposed to methyl acetate as used in Experiment F.

Experiment G

An experiment was performed with lithium iodide and hydrogen (both precharged to the autoclave prior to heating to reaction temperature) and a rhodium catalyst. Methyl acetate was used as a carbonylation feed and the water concentration decreased from 5.1 to 0.5% by weight as above. The rate of carbon monoxide uptake from the ballast vessel after 5 minutes was found to be 1773 mmol/hr. This is not according to the present invention as no dimethyl ether was used.

EXAMPLE 5

Experiment G was repeated (water concentration decreasing from 2.8 to 0.5% by weight as above) except that dimethyl ether was used as a feed. The rate of carbon monoxide uptake after 5 minutes was found to be 2100 mmol/hr. This is according to the present invention. The use of dimethyl ether enhances the carbonylation rate when compared with Experiment G.

The autoclave charges, reaction temperatures and pressures for Experiments F and G and Examples 4 and 5 are given in Table 3 and the analyses of the non-condensable gases vented from the autoclave at the end of the experiments are in Table 4.

TABLE 3

| Experiment | Feed | Temp (°C.) | Pressure (BarG) | Run Time (mins) | MeOAc (mmol) | DME (mmol) | MeI (mmol) | Water (mmol) | AcOH (mmol) | Ir (mmol) | Rh (mmol) | Hydrogen (BarG) | Li (mmol) |
|---|---|---|---|---|---|---|---|---|---|---|---|---|---|
| Experiment F | MeOAc | 185 | 34.8 | 34.5 | 777 | — | 82 | 583 | 1496 | 1.89[a] | — | — | — |
| Example 4 | DME | 185 | 34.8 | 25.8 | — | 386 | 85 | 200 | 2267 | 1.89[b] | — | — | — |
| Experiment G | MeOAc | 185 | 50 | 19.1 | 475 | — | 203 | 542 | 1505 | — | 0.40[c] | 1.5 | 149 |
| Example 5 | DME | 185 | 50 | 16.5 | — | 240 | 202 | 298 | 1979 | — | 0.40[d] | 1.6 | 148 |

[a] $H_2IrCl_6$ dissolved in 370 mmol $H_2O$
[b] $H_2IrCl_6$ dissolved in 364 mmol $H_2O$
[c] $Rh_2(CO)_4Cl_2$ dissolved in 117 mmol AcOH; 13 mmol MeOAc
[d] $Rh_2(CO)_4Cl_2$ dissolved in 133 mmol AcOH

TABLE 4

| Experiment | Methane (% v/v) | $CO_2$ (% v/v) | $H_2$ (% v/v) | DME (% v/v) |
|---|---|---|---|---|
| Experiment F | 6.03 | 3.0 | 4.0 | — |
| Example 4 | 0.9 | 4.0 | 1.77 | a |
| Experiment G | b | b | b | b |
| Example 5 | b | b | b | b |

Balance: Nitrogen and carbon monoxide.
[a] Dimethyl ether could not be accurately measured
[b] Not recorded.

We claim:

1. A process for the production of acetic acid which process comprises reacting carbon monoxide with a carbonylatable reactant introduced to a reactor in which there is maintained at elevated temperature a liquid reaction composition comprising a Group VIII noble metal catalyst, methyl iodide promoter, an optional co-promoter, and at least a finite concentration of water characterized in that the carbonylatable reactant comprises greater than 10% by weight dimethyl ether and the concentration of water in the liquid reaction composition is from 1.0 to 10% by weight.

2. A process according to claim 1 wherein the carbonylatable reactant comprises dimethyl ether together with methanol and/or methyl acetate.

3. A process according to claim 1 wherein the carbonylatable reactant comprises dimethyl ether and methanol which is obtained by reacting a mixture of carbon monoxide and hydrogen in the presence of a methanol synthesis catalyst and a methanol dehydration catalyst.

4. A process according to claim 1 wherein the concentration of water in the liquid reaction composition is in the range from 1 to 8% by weight.

5. A process according to claim 1 wherein the Group VIII noble metal catalyst in the liquid reaction composition comprises a rhodium-containing compound which is soluble in the reaction composition.

6. A process according to claim 5 wherein the concentration of the rhodium-containing compound in the liquid reaction composition is in the range 10 to 1500 ppm by weight of rhodium.

7. A process according to claim 1 wherein the Group VIII noble metal catalyst is rhodium and there is employed a co-promoter which is selected from ruthenium-, osmium-, rhenium-or manganese-containing compounds.

8. A process according to claim 1 wherein the Group VIII noble metal catalyst is rhodium and there is employed a co-promoter which is selected from the group consisting of Group IA and Group IIA metal iodides, quaternary ammonium iodides and phosphonium iodides.

9. A process according to claim 1 wherein the Group VIII noble metal catalyst in the liquid reaction composition comprises an iridium-containing compound which is soluble in the liquid reaction composition.

10. A process according to claim 9 wherein the concentration of the iridium-containing compound in the liquid reaction composition is in the range 100 to 6000 ppm by weight of iridium.

11. A process according to claim 1 wherein the Group VIII noble metal catalyst is iridium and there is employed a co-promoter which is selected from the group consisting of ruthenium, osmium, rhenium, cadmium, mercury zinc, gallium, indium and tungsten.

12. A process according to claim 1 wherein the carbonylatable reactant comprises between 30 and 100% by weight dimethyl ether.

* * * * *